United States Patent [19]

Meister et al.

[11] Patent Number: 5,152,297
[45] Date of Patent: Oct. 6, 1992

[54] METHOD AND APPARATUS FOR ESTABLISHING THE PRESSURE-DIAMETER RELATIONSHIP OF AN ARTERY BY NON-INVASIVE MEASURES

[75] Inventors: Jean-Jacques Meister, Epalinges; Yanik Tardy, Lausanne, both of Switzerland

[73] Assignee: Asulab SA, Bienne, Switzerland

[21] Appl. No.: 489,034

[22] Filed: Mar. 6, 1990

[30] Foreign Application Priority Data

Mar. 8, 1989 [CH] Switzerland ............... 855/89

[51] Int. Cl.$^5$ ............................................. A61B 5/02
[52] U.S. Cl. ..................... 128/672; 128/691; 128/694
[58] Field of Search ........... 128/660.04, 661.1, 661.05, 128/661.09, 672, 691, 694

[56] References Cited

U.S. PATENT DOCUMENTS

| | | | |
|---|---|---|---|
| 3,095,872 | 7/1963 | Tolles | 128/672 |
| 4,501,279 | 2/1985 | Seo | 128/663 |
| 4,562,843 | 1/1986 | Djordjevich et al. | 128/672 |
| 4,721,113 | 1/1988 | Stewart et al. | 128/661.04 |

FOREIGN PATENT DOCUMENTS 2481917 11/1981 France.

OTHER PUBLICATIONS

Nealeigh et al., "A Venous Pulse Doppler Catheter-Tip Flowmeter for Measuring Arterial Blood Velocity, Flow, and Diameter in Deep Arteries", ISA Trans., '76, pp. 84–87.

Langewouters et al., "The Static Elastic Properties of Human Thoracic and Abdominal Aortas in Vitro", Jul. 5, 1983, pp. 425–435.

Powalowski et al., "A Non-Invasive Ultrasonic Method for the Elasticity Evaluation of the Carotid Arteries", Nov. 5, 1987, pp. 109–126.

Medical & Biological Eng. & Com., vol. 16, No. 6, Nov. 1978, pp. 715–726.

IEEE Transaction on Biomedical Engineering, vol. BME-27, No. 3, Mar. 1980, pp. 150–155.

Primary Examiner—Stephen C. Pellegrino
Assistant Examiner—Steven J. Shumaker
Attorney, Agent, or Firm—Griffin, Branigan & Butler

[57] ABSTRACT

This method for establishing the pressure-diameter relationship of an artery employs the measurement results from a non-invasive sensor (3) of the artery diameter, for instance of the humeral artery, and from a non-invasive sensor (4) of the blood pressure applied for instance to the end of a finger. The measurement locations being separated by a distance $\Delta x$, the method provides for the correction of the pressure measurements as if such measurements had been effected at the location of the diameter measurements. The method further provides a correction which takes into account the mechanical properties of the artery, defined by the parameters $\alpha, \beta, \gamma, \ldots$ and which are calculated, if necessary by successive iterations, until the pressure-diameter curve appears free from all measurement anomalies (hysteresis). The pressure-diameter relationship enables the calculation of the mechanical properties of the artery, in particular by compliance curves and the propagation velocity as a function of the pressure.

16 Claims, 6 Drawing Sheets

METHOD AND APPARATUS FOR ESTABLISHING THE PRESSURE-DIAMETER RELATIONSHIP OF AN ARTERY BY NON-INVASIVE MEASURES

FIELD OF THE INVENTION

This invention concerns a method for establishing the pressure/diameter relationship of an artery at a given point of its course and an arrangement for carrying out this method.

BACKGROUND OF THE INVENTION

It is known that arterial compliance, which is to say the elastic behaviour of the artery, is considered as indispensable to good knowledge of the physiology, physiopathology and therapy of the arterial system. This compliance is a function of the arterial pressure and, in order to establish it, one thus needs to have the instantaneous relationship which exists between the pressure and the diameter at a given point of the artery.

Propositions for measuring the pressure-diameter relationship have already been advanced, for instance in the study presented on pages 789 to 793 of the review "Arch. Mal. Coeur Nr. 6, 1987, where the visco-elastic behaviour of the aorta on a conscious dog is analyzed. The viscoelastic response of the aorta to the administration of hormones is observed in the cited study by analyzing the aortic pressure-diameter relationship. This relationship is established by means of a pressure microsensor which may be calibrated in situ and introduced through the left humeral artery and placed in the light of the descending aorta and of two piezoelectric crystals of 4 mm diameter, diametrally attached in the envelope of the proximal descending aorta.

The means which have just been suggested have an invasive character, which is to say, they affect the integrity of the organs in which they intervene. On the contrary, the method of the present invention and the arrangement for carrying it out call for non-invasive sensors which remain placed at the surface of the artery to be analyzed with no penetration into the surrounding tissues.

Non-invasive sensors permitting the continuous measurement of blood pressure are known. In particular, one may mention the photoplethysmograph sold by the Ohmeda Company, 3030 Airco Drive, Madison, Wis., USA and bearing the registered trademark "finapres" (for finger arterial pressure). As indicated, the apparatus measures the blood pressure at the end of a finger according to the method described in the article "Effects of Peripheral Vasoconstriction on the Measurement of Blood Pressure in a Finger" in the review Cardiovascular Research, 1985, 19, 139–145.

Non-invasive sensors enabling the measurement of the arterial diameter are also known. In particular, there is the apparatus employed in the U.S. patent document U.S. Pat. No. 4,370,985 which permits the measurement of the arterial diameter by sending an ultrasonic wave onto the artery and measuring the echoes sent back by the walls thereof. This diameter measurement may be effected on surface arteries, for instance the humeral artery or the radial artery.

From the brief description of the presently known sensors which has just been given hereinabove, it is apparent that it is not possible to measure non-invasively the pressure in every artery other than that of the finger and the diameter of said artery at the same place in a manner such that the relationship or pressure-diameter curve shows systematic hysteresis. This is due to the fact that the wave propagation velocity being finite, the pressure variations measured downstream show a certain delay relative to the corresponding diameter. To be sure, this delay is greater when the distance which separates the two measurement sites increases. This measurement defect must be thus corrected in order that the mechanical properties of the artery calculated from the pressure-diameter relationship are not artificially distorted.

SUMMARY OF THE INVENTION

It is the purpose of this invention to provide a method for bringing the pressure measurements effected at one location of the arterial bed to another location where the diameter of the artery is measured. In order to effect this, the method is characterized by the following succession of steps:

(a) measuring non-invasively and simultaneously during at least one cardiac cycle, on one hand the diameter $D(t)$ of the artery at a first location and on the other hand the pressure $p(t)$ of the arterial bed at a second location, said first and second locations being assumed to be separated by a distance $\Delta x$, (b) memorizing at successive instants of the cardiac cycle pairs of values which include a diameter value $D(t)$ and a pressure value $p(t)$, (c) calculating on the basis of the thus memorized value pairs by a mathematical adjustment procedure the parameters $\alpha, \beta, \gamma, \ldots$ of a relationship of the diameter as a function of the pressure $D(p)=D(p, \alpha, \beta, \gamma, \ldots)$, such relationship being selected to take into account the behaviour of the artery, (d) calculating on the basis of said parameters and of each pressure value $p(t)$ initially measured, the propagation velocity $c(p)$ of the pressure wave generated by the cardiac function, (e) calculating for each value of propagation velocity $c(p)$ thus established and taking into account said distance $\Delta x$, the course time $\Delta t(p) = \Delta x/c(p)$ of the pressure wave between said first and second locations, (f) calculating for each pressure value $p(t)$ initially measured, a new pressure value $p[t+\Delta t(p)]$ prevailing at said first location and (g) establishing, with the aid of the diameter value $D(t)$ initially measured and said new pressure value at said first location, the pressure-diameter relationship $D(p)$ of said artery at said first location.

It is also the purpose of this invention to provide an arrangement for practising the method as defined hereinabove and this by means of sensors, a calculator and a visualization screen.

The invention will be understood now in the light of the description to follow given by way of example and in referring to the drawings.

BRIEF DESCRIPTION OF THE DRAWINGS

FIG. 1 is a schematic view of the measurement arrangement according to the invention showing an arm ending in a hand, the diameter sensor $D(t)$ and pressure sensor $p(t)$ being respectively arranged on the humeral artery of the arm and on one finger of the hand, and a calculator provided with a visualization screen;

DESCRIPTION OF THE PREFERRED EMBODIMENT

FIG. 1 is a schematic view of an arm 20 terminating with a hand 21. In this arm is to be found a superficial artery 22. The invention concerns the measurement of the pressure-diameter curve at a given point of the course of the artery. To effect this, there is placed at a first location 23 on the humeral artery a sensor 3 enabling measurement of the diameter D(t) of said artery. As has been mentioned hereinabove, this non-invasive sensor may be of the ultrasonic emission type which captures the echoes from the artery walls. One likewise places a sensor 4 enabling measurement of the pressure p(t) at a second location 25 at the end of a finger 26. This sensor is non-invasive and is of the plethysmograph type as suggested hereinabove. The measurement of the diameter and pressure are effected simultaneously during at least one cardiac cycle. The measurement locations 23 and 25 are separated by a distance Δx. The signals D(t) and p(t) issuing respectively from the sensors 3 and 4 are transmitted to a calculator 28 for processing. The calculator is completed by a visualization screen 29.

With the help of the arrangement which has just been described the method for establishing the pressure -diameter curve of an artery at a given point 23 in its course will now be explained with the help of the flow chart of FIG. 11 and the various diagrams shown on figures 2 to 8.

Figure 2:
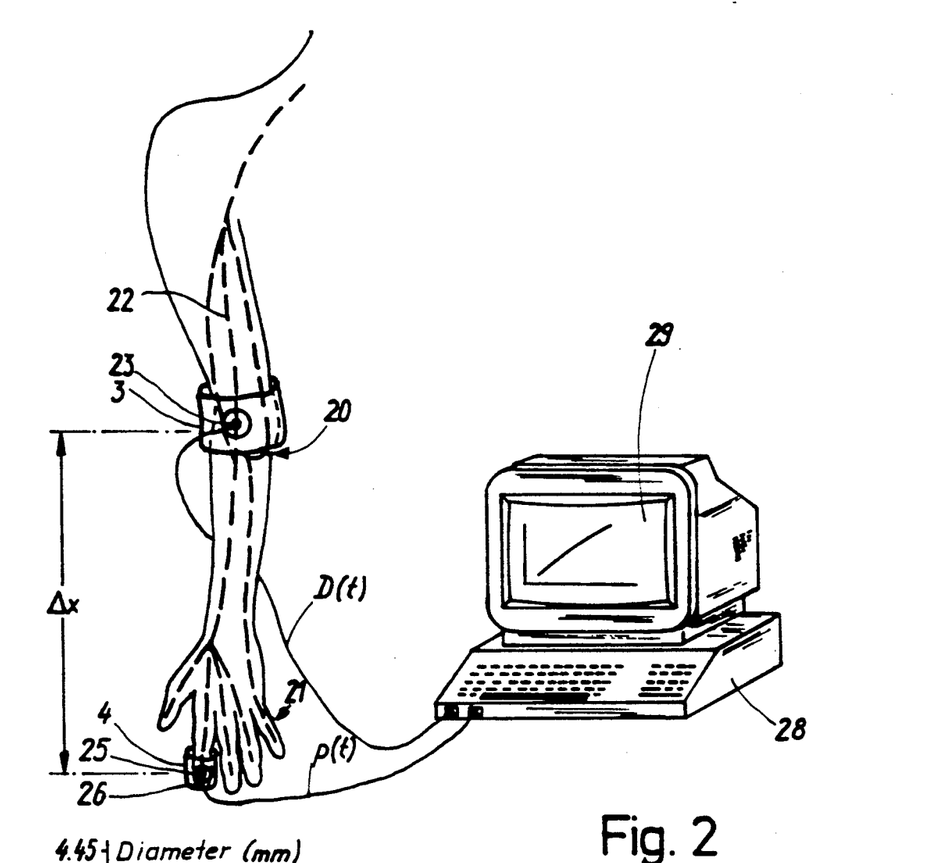
FIG. 2 is a diagram showing the signal $D(t)$ captured by the diameter sensor schematically shown on FIG. 1.
Figure 3:
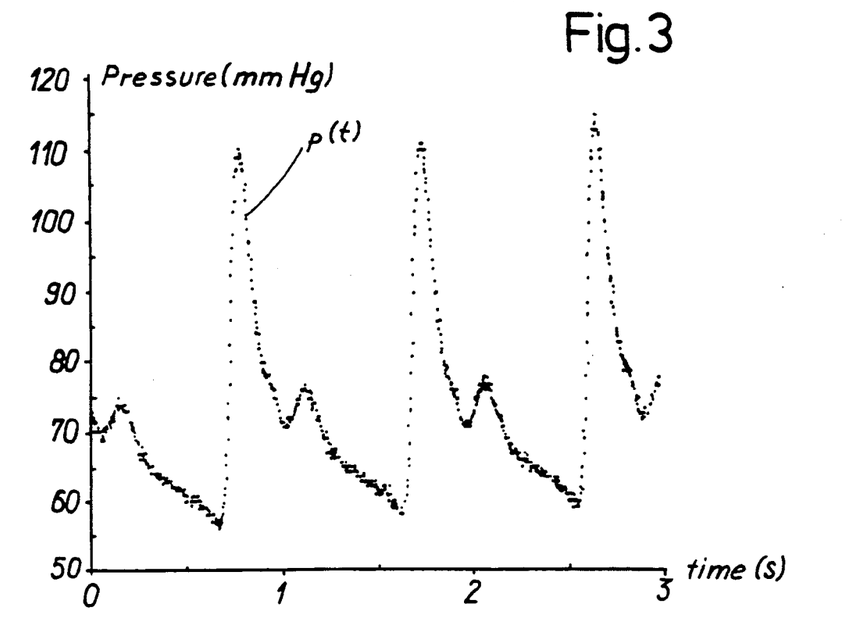
FIG. 3 is a diagram showing the signal p(t) captured by the pressure sensor schematically shown on FIG. 1.

FIG. 2 shows the signal D(t) issuing from the diameter sensor 3 where the values of the arterial diameter are shown as a function of time over about three cardiac cycles. Simultaneously with these diameter measurements, the pressure sensor 4 furnishes a signal p(t) likewise shown over about three cardiac cycles on FIG. 3, this signal giving pressure values as a function of time. It will here be recalled, and this for reasons given hereinabove, that the measurement of the diameter is effected at a first location 23 (on the humeral artery 22) and the pressure measurement is brought about at a second location 25 (at the end of the finger 26), these two locations being separated by the distance Δx. Thus, for a time value t1 one has available a pair of values D(t1) and p(t1) and one continues thusly for other time values.

Figure 4:
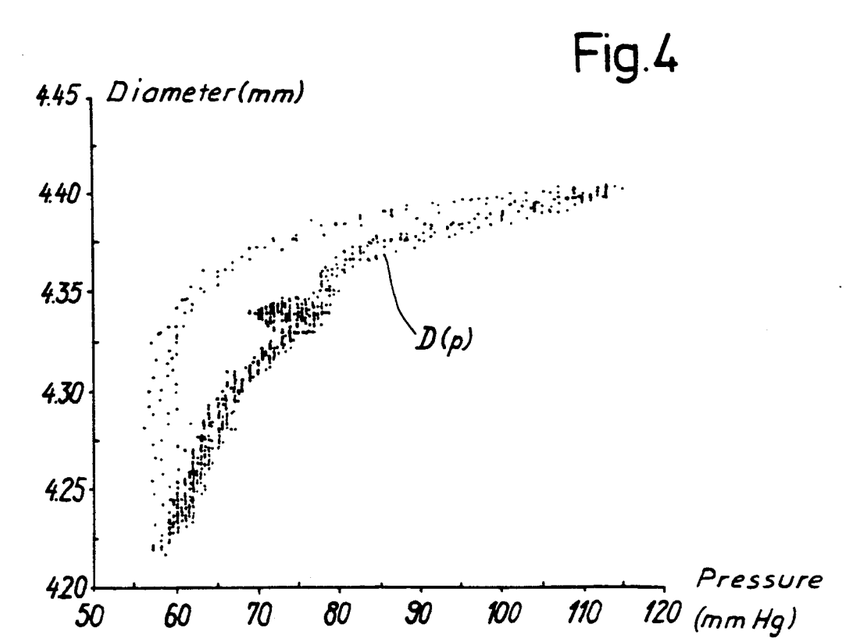
FIG. 4 is a diagram showing a set of points D(p) resulting from the combination of the diagrams of FIGS. 2 and 3.

Next one memorizes in calculator 28 and at successive instants t of the cardiac cycle the value pairs thus measured. Since at each instant one has available a pair of values D and p, it is now possible to establish a diagram wherein the diameter D is a function of the pressure p, the time variable having been eliminated. This diagram is shown on FIG. 4 where there appears a set of points D(p) showing a marked hysteresis due to the distance Δx which exists between the two measurement locations as has been explained hereinabove. The pressure-diameter diagram appearing on FIG. 4 is stored in the calculator 28 in block 5 thereof (FIG. 11). As required, this diagram may be visualized on screen 29.

There will now be calculated on the basis of the precedingly memorized value pairs, by a mathematical adjustment method, the parameters $\alpha, \beta, \gamma, \ldots$ of a relationship of the diameter as a function of the pressure $D(p) = D(p, \alpha, \beta, \gamma, \ldots)$, this relationship being chosen to take into account the behaviour of the artery.

Thus, one chooses initially a relationship D(p) relative to the pressure-diameter behaviour of the artery which one stores in the block 6 of calculator 28. This relationship is given by experience. It could take an exponential form:

$$p = \alpha e^{\frac{\beta \pi D^2}{4}}$$

in which D is the arterial diameter or again a form given in the review J. Biomechanics, vol. 17, Nr. 6, pp. 425-435, 1984 and which is written:

$$S = \alpha[\tfrac{1}{2} + \tan^{-1}[(p-\beta)/\gamma]/\pi$$

where S is the cross-section of the artery $\alpha$ is its maximal area, p is the transmural pressure, $\beta$ is the pressure at which compliance is maximal, and $\gamma$ is the half width pressure. In the numerous relationships proposed in the literature, the number of parameters $\alpha, \beta, \gamma, \ldots$ is variable.

Having chosen the relationship $D(p) = D(p, \alpha, \beta, \gamma, \ldots)$ which suits, one will now proceed to its adjustment on the value pairs previously obtained, and this by means of a mathematical adjustment method or routine known from the state of the art, for instance the least squares method. Other methods are possible and are described in detail in the work "Numerical Recipes" published by "The Press Syndicate of the University of Cambridge" 1986. Very generally, it concerns a standard mathematical procedure for minimization of spreads.

Figure 5:
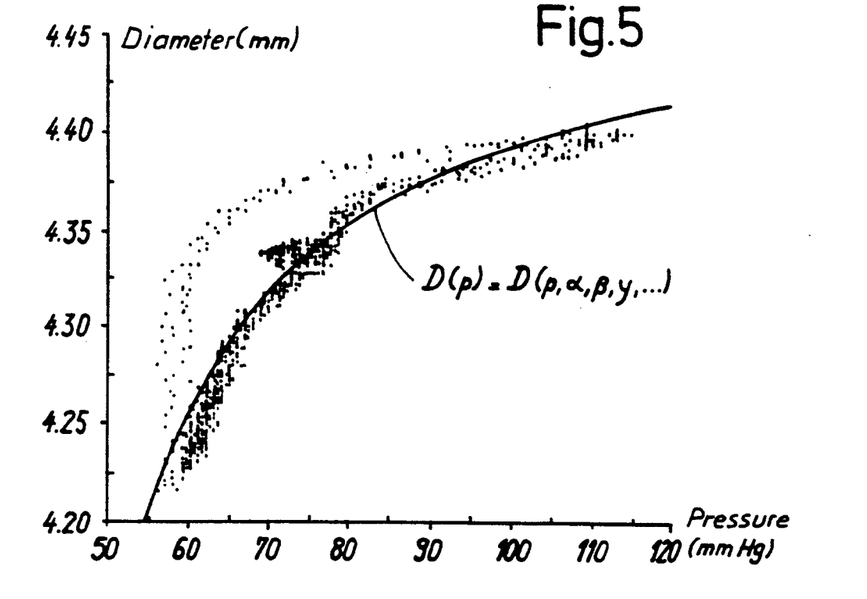
FIG. 5 is a diagram showing a curve resulting from an adjustment applied to the set of points of the diagram of FIG. 4.
Figure 11:
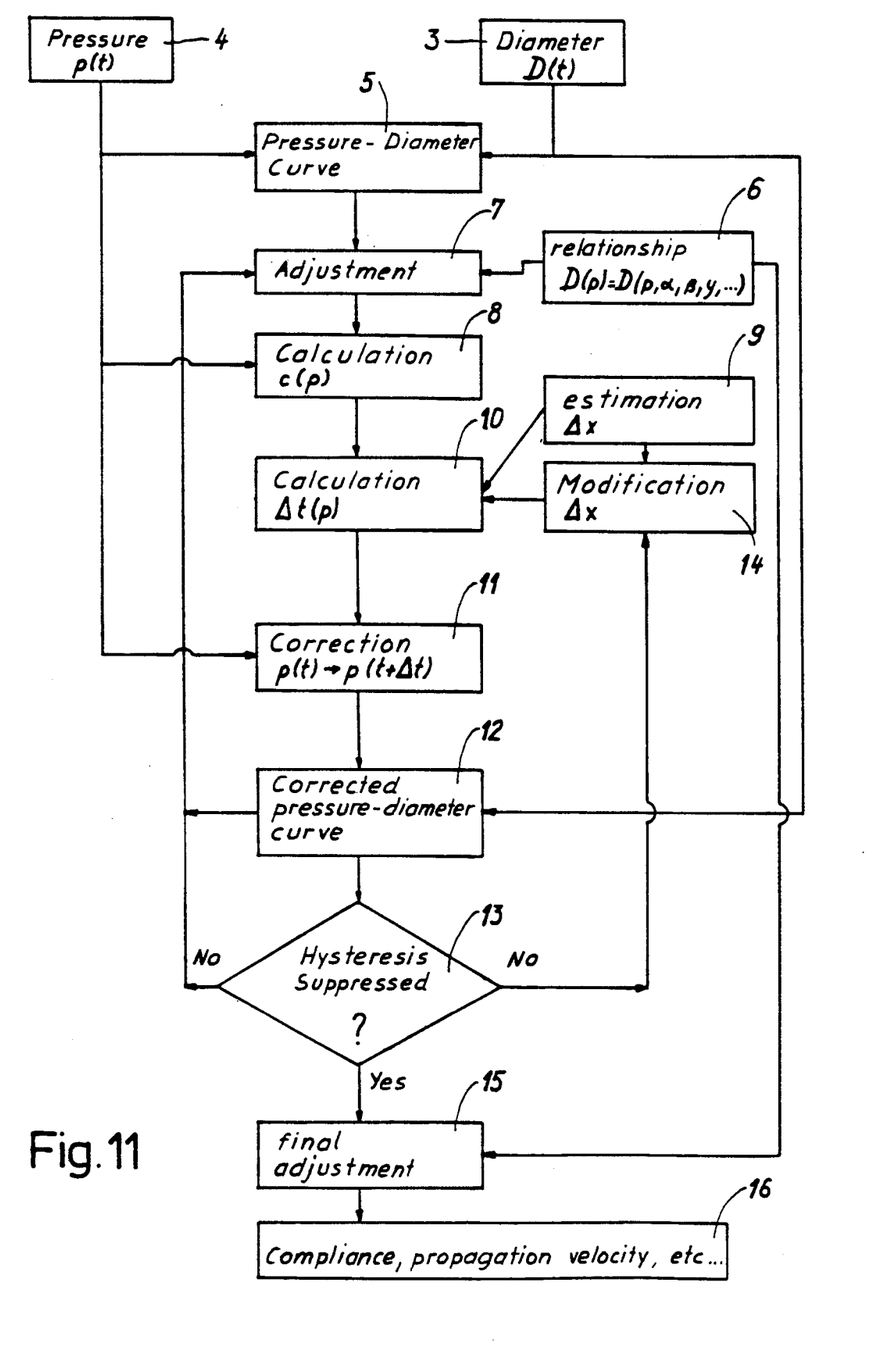
FIG. 11 is a flow chart showing how the several steps of the method according to the invention are connected together.

This adjustment (or "fit"), which is symbolized by block 7 of the flow chart of FIG. 11, gives rise to the pressure-diameter curve D(p) $D(p, \alpha, \beta, \gamma, \ldots)$ drawn on FIG. 5, this curve being determined by the parameters $\alpha, \beta, \gamma, \ldots$ The following step (block 8 of the flow chart of FIG. 11) enables calculation from the parameters $\alpha, \beta, \gamma, \ldots$ previously obtained and for each pressure value p(t) initially measured (block 4), the propagation velocity c(p) of the pressure wave generated by the cardiac function. The velocity c(p) may be obtained for instance in employing its expression known from the study of arterial haemodynamics and which is written $$c(p) = \sqrt{\frac{S}{\rho} \cdot \frac{dp}{dS}}$$

wherein $\rho$ is the blood density, $$S = \frac{\pi D^2}{4}$$

is the cross-section of the artery and wherein dp/dS is the derivative of the pressure by the cross-section.

Next one calculates for each propagation velocity value c(p) obtained in the previous step and taking into account the distance $\Delta x$ separating the first and second measurement locations (23 and 25 on FIG. 1), the time $$\Delta t(p) = \Delta x / c(p)$$

which the pressure wave requires to traverse the said distance $\Delta x$. This calculation is effected by block 10. Here there will be noted that the distance $\Delta x$ is given by estimation (block 9). An approximate value of this $\Delta x$ is obtained in measuring exteriorly the distance which separates the two measurement sites.

For each pressure value p(t) initially measured (block 4), one next calculates a new value of the pressure $p[t + \Delta t(p)]$ prevailing or, in other terms, brought back to the first location and which expresses the value of the pressure which one would have measured at this first location, had it been possible there to place the pressure sensor. This correction is effected on block 11 of the flow chart of FIG. 11.

Finally, one establishes with the help of the diameter value D(t) initially measured at the first location (block 3) and the new pressure value $p[t + \Delta t(p)]$ previously obtained, the pressure-diameter relationship D(p) at the first location 23. This curve is presented on block 12.

The successive steps which have been explained hereinabove thus give the complete method as claimed in the present invention according to the first claim and which enables measurement of the pressure-diameter relationship of an artery at a given point of its course, even though at least one of these measurements is not effected at this point.

Figure 7:
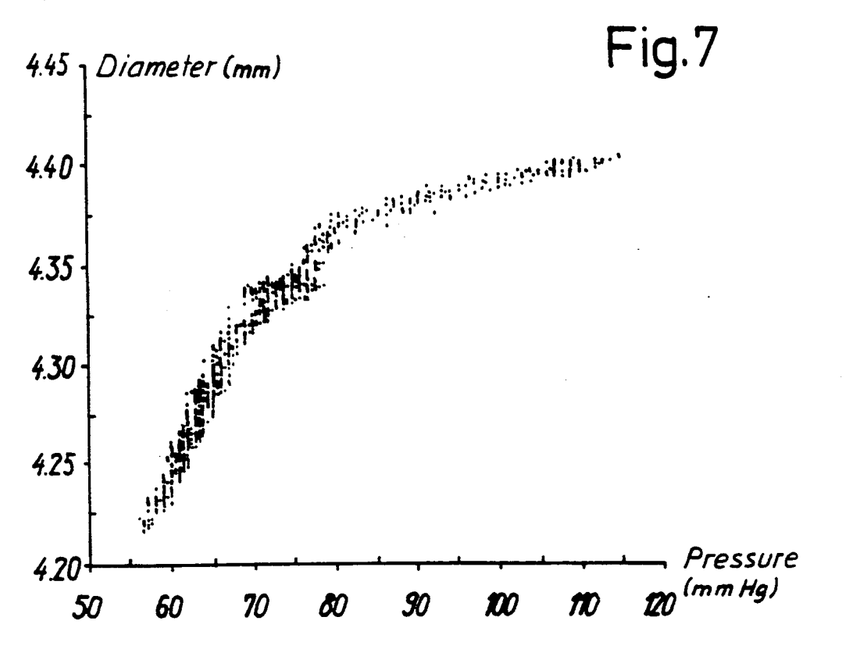
FIG. 7 is a diagram showing a set of points D(p) for which the pressure measurement p(t) has been brought back to the location of the diameter measurement, this set showing an optimum correction.

Here it will be noted that the pressure-diameter curve obtained in block 12 is a set of points which may be presented in various fashions. FIG. 7 shows a graph no longer exhibiting hysteresis. The correction is thus considered optimum. In these conditions, block 13 referred to as the decision block, proceeds to a final adjustment (block 15) utilizing once again a standard mathematical method for minimization of spreads as described hereinabove. One derives then from this adjustment the definitive values of the parameters $\alpha, \beta, \gamma, \ldots$ characteristic of the observed artery. The final adjustment is shown by the full curve A of FIG. 8 which appears as an average superposed on the set of points of FIG. 7 and taken up in FIG. 8.

Figure 8:
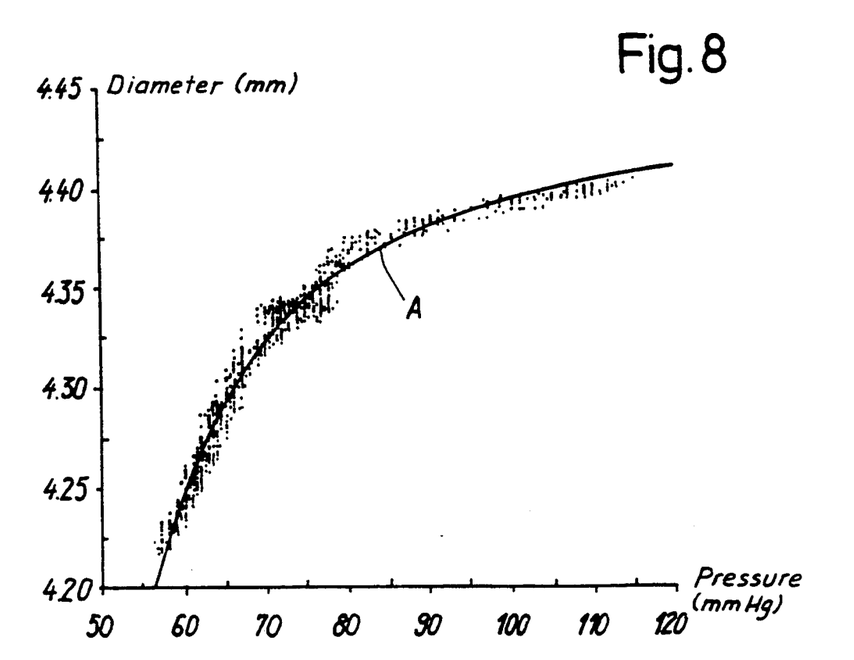
FIG. 8 takes up the set of points D(p) shown on FIG. 7 from which set one obtains the definitive pressure-diameter curve.
Figure 9:
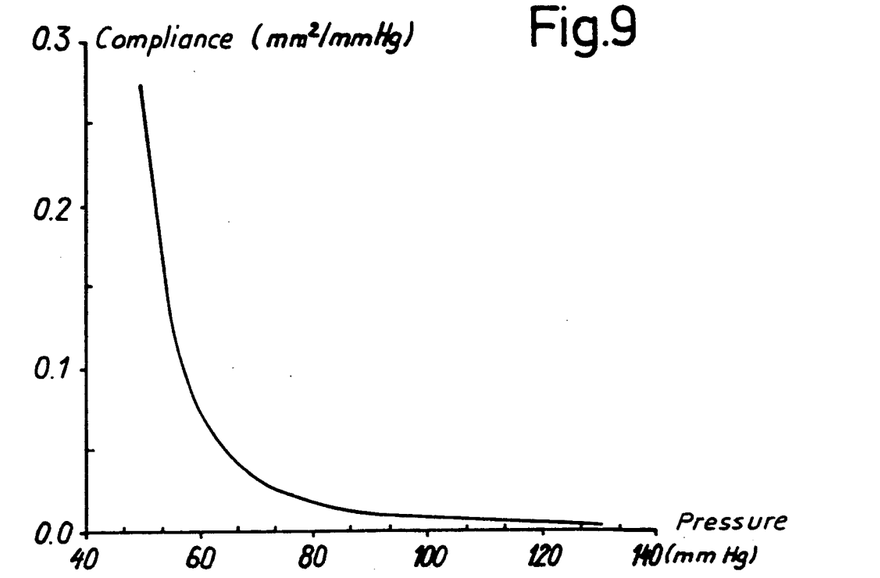
FIG. 9 is a diagram representing the arterial compliance as a function of the pressure, such diagram resulting from the curve obtained in FIG. 8.
Figure 10:
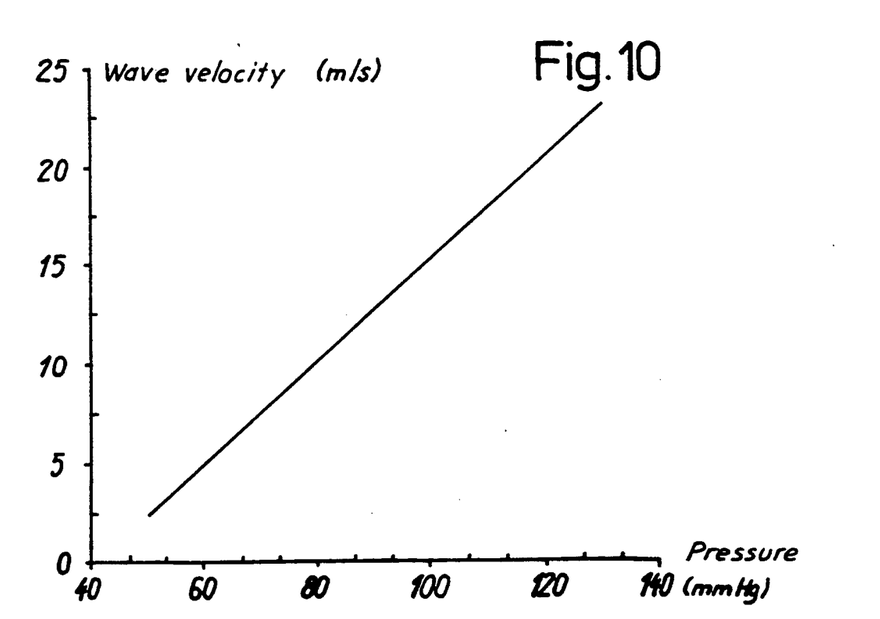
FIG. 10 is a diagram representing the velocity of the pressure wave as a function of the pressure, such diagram resulting from the curve obtained in FIG. 8.

The calculation of the mechanical properties of the artery is then effected from curve A of FIG. 8 (block 16). From this curve may be deduced the compliance (figure 9) defined by the relationship dS/dp, which is nothing other than the slope of curve A and the propagation velocity of the pressure wave c(p) (FIG. 10).

Figure 6:
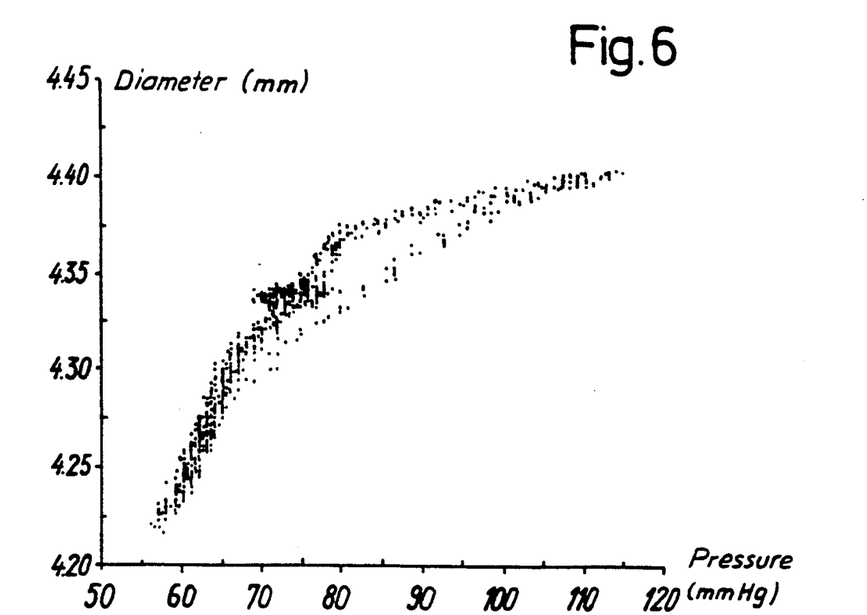
FIG. 6 is a diagram showing a set of points D(p) for which the pressure measurement p(t) has been brought back to the location of the diameter measurement, this set showing a correction which is not optimum.

The pressure-diameter curve obtained in block 12 may still exhibit a certain hysteresis as is the case in the set of points shown on FIG. 6. In this case the decision block 13 will judge the correction as non-optimum. The values obtained in block 12 will then form the object of a new adjustment taking up once again the method described from block 7 on and in running once again through the steps of block 8 to 12, and this as often as the dispersion of the value pairs obtained following the step symbolized by block 12 does not satisfy a predetermined criterion which in fact is the disappearance of the hysteresis. One thus proceeds here by successive iterations.

The hysteresis may further be corrected in another manner, namely by modifying the initially estimated value of $\Delta x$ (block 9). If the decision element 13 shows a non-suppressed hysteresis, the calculator may modify the value of $\Delta x$ (block 14) and introduce it from the step calculating the delay $\Delta x$ (block 10). At this moment the calculation is taken up again from block 10. It is evident that one may combine the modification of $\Delta x$ and the adjustment practised from block 7 on.

It is further mentioned that all the steps of the method of the invention as well as the calculations which appear on the flow chart of FIG. 11 may be effected by means of a computer sold on the market for instance by the computer Olivetti M28. In the same manner as has been mentioned hereinabove in respect of block 5, the visualization screen enables showing on demand any of the graphics of the method should the operating practitioner judge it necessary.

What we claim is:

1. A method for establishing the pressure-diameter relationship of an artery at a given point in its course including the following succession of steps:

(a) measuring non-invasively and simultansouely during at least one cardiac cycle the diameter D(t) of the artery at a first location and the pressure p(t) of the arterial bed at a second location separated from said first location by an unknown distance $\Delta x$, to generate electrical signals representing said diameter and said pressure, said measuring of said diameter comprising directing ultrasonic waves toward said artery at said first location and sensing echoes of said waves reflected from a wall of said artery to produce the electrical signal representing said artery diameter the pressure measurement signal produced by a non-evasive blood pressure sensor means, (b) storing in a memory device at successive instants of the cardiac cycle pairs of values representing said signals, each pair of values including a diameter value D(t) and a pressure value p(t), said pairs of values exhibiting a dispersion due to the fact that said diameter is measured at said first location and said pressure is measured at said second location, (c) calculating on the basis of the stored pairs of values by a mathematical adjustment procedure the parameters $\alpha, \beta, \gamma, \ldots$ of a relationsip of the diameter as a function of the pressure $D(p) = D(p, \alpha, \beta, \gamma, \ldots)$, where $\alpha, \beta, \gamma, \ldots$ are parameters expressing the behavior of the artery and p represents pressure, (d) calculating on the basis of said parameters and of each pressure value p(t) initially measured, the propagation velocity c(p) of the pressure wave generated by the cardiac function, (e) calculating for each value of propagation velocity c(p) thus calculated and taking into account said distance Δx, the course time Δt(p)=Δx/c(p) of the pressure wave between said first and second locations, (f) calculating for each pressure value p(t) initially measured, a new pressure value [p[t+Δt(p)]] p(t+Δt(p)) prevailing at said first location and (g) establishing, from the diameter value D(t) initially measured and said new pressure values at said first location, new pairs of values representing the pressure-diameter relationship of said artery at said first location.

2. A method as set forth in claim 1 in which (h) steps (c) to (g) are repeated until the dispersion of the pairs of values obtained following step (g) satisfy a predetermined criterion.

3. A method as set forth in claim 2 wherein step (h) is effected by using again the values obtained following step g.

4. A method as set forth in claim 2 wherein step (h) is effected by using again the values acquired following step (g) and modifying the value of said distance Δx assumed in proceeding with the calculation indicated during step (e).

5. A method as set forth in claim 4 wherien (i) steps (e) to (g) are repeated until the dispersion of the new pairs of values obtained following step (g) satisfy a predetermined criterion in modifying the value of said assumed distance Δx.

6. A method as set forth in claim 1 wherein the propagation velocity c(p) of step (d), is calculated according to the expression $$c(p) = \sqrt{\frac{S}{\rho} \cdot \frac{dp}{dS}}$$

where $$S = \frac{\pi D^2}{4}$$

and ρ is the density of the blood.

7. A method as set forth in claim 1 wherein at least some of the results of said calculations are visualized on a screen.

8. A method as set forth in claim 1 which includes the step of displaying said apirs of values on a visualization screen.

9. A method for establishing the press-diameter relationship of an artery at a given location in its course, said method comprising the following steps:

(a) disposing first and second sensor means outside said artery at first and second locations separated by an unknown distance assumed to be a distance ΔX;

(b) energizing said sensor means whereby one of said sensor means produces an electrical output signal representing the diameter of said artery at one of said locations and the other of said sensor means produces an electrical output signal representing the pressure of the arterial bed at the other of said locations;

(c) repeatedly and simultaneously sampling said output signals from said sensor means over an interval including at least one cardiac cycle to produce electrical signals representing pairs of values, each pair of values including a diameter value D(t5) and a pressure value p(t) and exhibiting a dispersion due to the fact that said diameter and pressure are measured at said first and second locations;

(d) storing said pairs of values in a computer memory;

(e) determining from said stored pairs of values by a mathematical adjustment procedure the parameters, α, β, γ, ... of a relationship of the diameter as a function of the pressure D(p)=D(p, α, β, γ, ... ). where α, β, γ, ... are parameters expressing behavior of the artery, (f) calculating from said parameters and each pressure value p(t) initially measured, the propagation velocity c(p) of the pressure wave generated by the cardiac function, (g) calculating for each value of propagation velocity c(p) thus established and taking into account said distance Δx, the course time Δt(p)=Δx/c(p) of the pressure wave between said first and second locations, (h) calculating for each pressure value p(t) initially measured, a new pressure value p(t+Δt(p)) [p[t+Δt(p)]] prevailing at said first location and, (i) establishing, from the diameter values D(t) initially sampled and said new pressure values at said first location, new pairs of values representing the pressure-diameter relationship of said artery at said first location.

10. A method as set forth in claim 9 in which (j) steps (e) to (i) are repeated until the dispersion of the new pairs of values established in step (i) satisfy a predetermined criterion.

11. A method as set forth in claim 10 wherein step (j) is effected by using the values established in step (i) and by modifying the value of said assumed distance Δx in proceeding with the calculation step (g).

12. A method as set forth in claim 11 wherein (j) steps (g) and (i) are repeated until the dispersion of the pairs of values obtained following step (g) satisfy a predetermined criterion in modifying the value of said assumed distance Δx.

13. A method as set forth in claim 9 wherein the propagation velocity c(p) of step (f), is calculated according to the expression $$c(p) = \sqrt{\frac{S}{\rho} \cdot \frac{dp}{dS}}$$

where $$S = \frac{\pi D^2}{4}$$

and ρ]is the density of the blood.

14. A method as set forth in claim 9 and further comprising the step of displaying the results of at least some said calculations on a screen.

15. Apparatus for establishing the pressure-diameter relationship of an artery at a given point in its course, said apapratus comprising:

(a) first and second sensor means disposed outside said artery at first and second locations spearated by an unknown distance assumed to be a distance ΔX, one of said sensor means producing an electrical output signal representing the diameter of said artery at one of said locations and the other of said sensor means producing an electrical output signal representing the pressure of the arterial bed at the other of said locations;

(b) means for repeatedly and simultaneously sampling said output signals from said sensor means over an interval including at least one cardiac cycle to produce electrical signals representing pairs of values, each pair of values including a diameter value D(t) and a pressure value p(t) and exhibiting a dispersion due to the fact that said diameter and pressure are measured at said first and second locations;

(c) a computer memory for storing said pairs of values; and, (d) a computer, said computer including, first means for calculating on the basis of the stored pairs of values by a mathematical adjustment procedure the parameters $\alpha, \beta, \gamma, \ldots$ of a relationship of the diameter as a function of the pressure $D(p) = D(P, \alpha, \beta, \gamma, \ldots)$, where said parameters express behvaior of the artery, second means responsive to said first means and said computer memory for calculating from said parameters and each pressure value p(t) initially measured, the propagation velocity c(p) of the pressure wave generated by the cardiac function, third means responsive to said second means for calculating from each value of propagation velocity c(p) thus calculated and a value representing said distance $\Delta x$, the course time $\Delta t(p) = \Delta x/c(p)$ of the pressure wave between said first and second locations, fourth means responsive to said third means for calculatiogn for each pressure value p(t) initially measured, a new pressure value $[p[t+\Delta t(p)]]$ $p(t+\Delta t(p))$ prevailing at said first location, and means responsive to said fourth means for establishing from the diameter values D(t) initially sampled and said new pressure values at said first location, new pairs of values representing the pressure-diameter relationsihp of said artery at said first location.

16. Apparatus as claimed in claim 15 and further comprising means for visually displaying said pressure-diameter relationship.

* * * * *